(12) United States Patent
Itatani et al.

(10) Patent No.: US 8,624,060 B2
(45) Date of Patent: Jan. 7, 2014

(54) PROCESS FOR PREPARING FLUOROCARBOXYLIC ACID

(75) Inventors: Shuji Itatani, Settsu (JP); Takuya Ichida, Settsu (JP); Noriaki Shibata, Settsu (JP); Kaori Ohno, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 366 days.

(21) Appl. No.: 13/055,095

(22) PCT Filed: Sep. 4, 2009

(86) PCT No.: PCT/JP2009/065879
§ 371 (c)(1),
(2), (4) Date: Jan. 20, 2011

(87) PCT Pub. No.: WO2010/027103
PCT Pub. Date: Mar. 11, 2010

(65) Prior Publication Data
US 2011/0124915 A1 May 26, 2011

Related U.S. Application Data

(60) Provisional application No. 61/095,107, filed on Sep. 8, 2008.

(51) Int. Cl.
*C07C 51/48* (2006.01)
*C07C 53/21* (2006.01)
*C07C 59/135* (2006.01)

(52) U.S. Cl.
USPC ....................................................... 562/605

(58) Field of Classification Search
None
See application file for complete search history.

(56) References Cited

U.S. PATENT DOCUMENTS

| 4,542,238 | A | 9/1985 | Ishikawa |
| 4,889,656 | A | 12/1989 | Flynn et al. |
| 5,312,935 | A | 5/1994 | Mayer et al. |
| 7,126,016 | B2 * | 10/2006 | Fu et al. ........................ 554/154 |
| 7,253,315 | B2 * | 8/2007 | Fu et al. ........................ 562/602 |
| 2003/0168405 | A1 | 9/2003 | Ichida et al. |
| 2005/0165254 | A1 | 7/2005 | Fu et al. |
| 2005/0171381 | A1 | 8/2005 | Fu et al. |

FOREIGN PATENT DOCUMENTS

| CA | 2067077 A1 | 10/1992 |
| CA | 2094557 | 10/1993 |
| CA | 1324135 | 11/1993 |
| CN | 1684934 A | 10/2005 |
| CN | 1684937 A | 10/2005 |
| EP | 0081053 A1 | 6/1983 |
| EP | 0314380 A1 | 5/1989 |
| EP | 0510596 A2 | 10/1992 |
| EP | 0566974 A1 | 10/1993 |
| EP | 1323460 A1 | 7/2003 |
| EP | 1542957 B9 | 9/2009 |
| EP | 1546081 B1 | 12/2012 |
| GB | 1194431 | 6/1970 |
| JP | 48-7086 | 3/1973 |
| JP | 58-57333 A | 4/1983 |
| JP | 1-157932 A | 6/1989 |
| JP | 6-25072 A | 2/1994 |
| JP | 06-128189 A | 5/1994 |
| JP | 2002-58966 A | 2/2002 |
| JP | 2006-500423 A | 1/2006 |
| JP | 2006-501300 A | 1/2006 |
| JP | 2007-99624 A | 4/2007 |
| WO | 2004/031141 A2 | 4/2004 |
| WO | WO 2004029008 A2 | 4/2004 |

* cited by examiner

*Primary Examiner* — Yevegeny Valenrod

(74) *Attorney, Agent, or Firm* — Sughrue Mion, PLLC

(57) ABSTRACT

A process for preparing a fluorocarboxylic acid, which includes a dehydration step of removing from a mixture containing a fluorocarboxylic acid and water at least a part of the water to obtain a dehydrated fluorocarboxylic acid solution, and a purification step of purifying the dehydrated fluorocarboxylic acid solution.

4 Claims, 2 Drawing Sheets

PROCESS FOR PREPARING FLUOROCARBOXYLIC ACID

CROSS-REFERENCE TO RELATED APPLICATIONS

This Application claims benefit under 35 U.S.C. §119(e) of U.S. Provisional Application No. 61/095,107 filed Sep. 8, 2008, incorporated herein by reference in its entirety.

TECHNICAL FIELD

The present invention relates to a process for preparing a fluorocarboxylic acid. More particularly, it relates to a process for preparing a fluorocarboxylic acid in high purity and in high yield.

BACKGROUND ART

Fluorocarboxylic acids, such as $C_8$ fluorocarboxylic acids and their salts, are known to have excellent chemical stability based on good heat resistance, chemical resistance, and oxidation resistance, in addition to good surface activity. These fluorocarboxylic acids, as well as their ammonium salts and metal salts, are widely known as surfactants used for polymerization of fluoroolefins such as tetrafluoroethylene, surfactants for an aqueous dispersion, and water and oil repellents. It is well known that such fluorocarboxylic acids are generally prepared by hydrolyzing the corresponding fluorocarboxylic acid fluorides.

The following process can be cited as an example of a process for preparing fluorocarboxylic acids. That is, the process comprises the steps of hydrolyzing fluorocarboxylic acid fluorides in the presence of a sulfuric acid aqueous solution to form a reaction product containing fluorocarboxylic acids and hydrogen fluorides, and removing at least some of the hydrofluoric acids from the reaction product by washing the reaction product with the sulfuric acid aqueous solution (for example, see Patent Document 1). In this method, at a temperature equal to or higher than the melting point of fluorocarboxylic acids, fluorocarboxylic acids are rendered into a molten state and separated into a hydrogen fluoride-containing sulfuric acid aqueous phase and a fluorocarboxylic acid-containing organic phase based on the low solubility of the fluorocarboxylic acids to the sulfuric acid aqueous solution. As a result, a fluorocarboxylic acid phase is obtained. Distillation is carried out on the fluorocarboxylic acid phase, so that fluorocarboxilic acids can be obtained in comparatively high purity.

In addition, the above fluorocarboxylic acids can be prepared by recovering and regenerating the fluorocarboxylic acids after used in surfactants for polymerization (for example, see Patent Document 2).

Patent Document 1: JP-W 2006-500423
Patent Document 2: JP-W 2006-501300

SUMMARY OF THE INVENTION

There is a need for a process for preparing fluorocarboxylic acids in higher purity and in higher yield compared to those achieved in the conventional process for preparing fluorocarboxylic acids. Accordingly, the object of the present invention is to provide a process for industrially preparing a fluorocarboxylic acid in high purity and in high yield.

The present invention is a process for preparing a fluorocarboxylic acid, which comprises:

a dehydration step of removing from a mixture containing a fluorocarboxylic acid and water at least apart of said water to obtain a dehydrated fluorocarboxylic acid solution; and a purification step of purifying said dehydrated fluorocarboxylic acid solution.

The present invention is specifically described in the following.

The process disclosed in Patent Document 1 includes separation of a sulfuric acid aqueous phase from a fluorocarboxylic acid phase (hereinafter, referred to as liquid-liquid separation). As above described, fluorocarboxylic acids obtained through this liquid-liquid separation may be further subjected to a simple distillation, so that fluorocarboxylic acids can be obtained in comparatively high purity. However, there has been a problem that achieving the higher purity significantly lowers the yield. On the other hand, there has been a problem that achieving the higher yield lowers the purity. Such behavior can be seen also in the fluorocarboxylic acids obtained by the process for preparing fluorocarboxylic acids by recovering and regenerating the same, which is disclosed in Patent Document 2.

Research to clarify the reason for this has brought the inventors to reach the below presumption. Fluorocarboxylic acids obtained by the above liquid-liquid separation contain at least a few percents of water. Here, the fluorocarboxylic acids azeotrope with water, and form gel with water over a wide range in composition. Consequently, distillation presumably tends to be unstable. In addition, coexistence of water and the fluorocarboxylic acids having surface active properties presumably prevents purification, for example, by generating bubbles inside a distillation column.

Based on these findings, the inventors have found out that preparation of fluorocarboxylic acids in high purity and in high yield is enabled by a dehydration step for obtaining a dehydrated fluorocarboxylic acid solution by removing at least a part of water contained in a mixture. Accordingly, the inventors have completed the present invention.

According to the process of the present invention, it is possible to prepare a fluorocarboxylic acid in high yield, without lowering the purity.

As the above-mentioned fluorocarboxylic acid, there may be mentioned fluoroethercarboxylic acids represented by the general formula (i)

wherein X is a H, F, or Cl, and Rf is a linear or branched fluoroalkylene group containing 4 to 14 carbon atoms, preferably 5 to 7 carbon atoms. Examples of Rf include a linear or branched fluoroalkylene group containing 7 carbon atoms, and particularly, a linear or branched perfluoroalkylene group.

Examples of compounds represented by the general formula (i) include $C_5F_{11}COOH$, $C_6F_{13}COOH$, and $C_7F_{15}COOH$. In particular, $C_5F_{11}COOH$ is desirable because it can be highly dehydrated, so that the compound in high purity is obtained ultimately.

As the above-mentioned fluorocarboxylic acid, there may also be mentioned fluoroethercarboxylic acids represented by the general formula (ii):

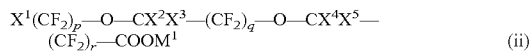

in which $X^1$, $X^2$, $X^3$, $X^4$ and $X^5$ are the same or different and each represents a H, F or $CF_3$; $M^1$ represents monovalent alkali metal, $NH_4$ or H; p represents 1 or 2; q represents 1 or 2; r represents 0, 1 or 2. As a fluoroethercarboxylic acid represented by the general formula (ii), there may be mentioned CF$_3$OCF(CF$_3$)CF$_2$OCF(CF$_3$)COONH$_4$, CF$_3$CF$_2$OCF$_2$CF$_2$OCF$_2$COONH$_4$, CF$_3$OCF$_2$CF$_2$CF$_2$OCHFCF$_2$COONH$_4$, for instance.

As the above-mentioned fluorocarboxylic acid, there may also be mentioned fluoroethercarboxylic acids represented by the general formula (iii):

$$X—(CF_2)_m—O—(CF(CF_3)CF_2O)_n—CF(CF_3)COOH \quad (iii)$$

wherein X is a H, F, or Cl, m is an integer from 1 to 10, such as 5, and n is an integer from 0 to 5, such as 1.

Desirable examples of compounds represented by the general formula (iii) include CF$_3$—O—CF(CF$_3$)CF$_2$O—CF(CF$_3$)COOH.

As the above-mentioned fluorocarboxylic acid, there may also be mentioned fluoroethercarboxylic acids represented by the general formula (iv):

$$X—(CF_2)_m—O—(CF(CF_3)CF_2O)_n—CHFCF_2COOH \quad (iv)$$

wherein X, m, and n are defined as above.

As the above-mentioned fluorocarboxylic acid, there may also be mentioned fluoroethercarboxylic acids represented by the general formula (v):

$$X—(CF_2)_m—O—(CF(CF_3)CF_2O)_n—CH_2CF_2COOH \quad (v)$$

wherein X, m, and n are defined as above.

As the above-mentioned fluorocarboxylic acid, there may also be mentioned fluoroethercarboxylic acids represented by the general formula (vi):

$$Rf^3OCF_2CF_2O(CF_2)_pCOOM^1 \quad (vi)$$

wherein Rf$^3$ represents a partially or wholly fluorine-substituted alkyl group, M$^1$ represents a monovalent alkali metal, NH$_4$ or H, p represents 1 or 2. Rf$^3$ is preferably an alkyl group containing 1 to 3 carbon atoms. As a fluoroethercarboxylic acid represented by the general formula (vi), there may be mentioned CF$_3$CF$_2$OCF$_2$CF$_2$OCF$_2$COONH$_4$, CF$_3$CF$_2$OCF$_2$CF$_2$OCF$_2$COOH, for instance.

As the above-mentioned fluorocarboxylic acid, there may also be mentioned fluoroethercarboxylic acids represented by the general formula (vii):

$$Rf^4OCHFCF_2COOM^1 \quad (vii)$$

wherein Rf$^4$ represents a linear partially or wholly fluorine-substituted aliphatic group or a linear partially or wholly fluorine-substituted aliphatic group interrupted with one or more oxygen atoms, M$^1$ represents a monovalent alkali metal, NH$_4$ or H. Rf$^4$ is preferably an aliphatic group containing 1 to 3 carbon atoms. As a fluoroethercarboxylic acid represented by the general formula (vii), there may be mentioned CF$_3$CF$_2$OCF$_2$CF$_2$OCF$_2$COONH$_4$, CF$_3$CF$_2$OCF$_2$CF$_2$OCF$_2$COOH, for instance.

The preparation process of the present invention comprises a dehydration step of removing, from a mixture containing a fluorocarboxylic acid and water, at least a part of the water to obtain a dehydrated fluorocarboxylic acid solution.

The dehydration step desirably includes adding concentrated sulfuric acid to the mixture containing a fluorocarboxylic acid and water. Addition of concentrated sulfuric acid advances the dehydration quite effectively.

Solubility of a fluorocarboxylic acid to concentrated sulfuric acid and solubility of concentrated sulfuric acid to a fluorocarboxylic acid are both low. That means fine separability between a fluorocarboxylic acid phase and a concentrated sulfuric acid phase. The system allowed to stand easily forms a phase interface, and is separated into an aqueous phase mainly containing sulfuric acid and an organic phase mainly containing a fluorocarboxylic acid. Accordingly, the dehydration step proceeds in a liquid (aqueous phase)-liquid (organic phase) heterophase dispersed (or mixed) system at any stage in the process from the addition of concentrated sulfuric acid to the completion of a dehydration reaction. The amount of the fluorocarboxylic acid in the organic phase is not particularly limited, and is desirably 80% by mass or more, and is more desirably 90% by mass or more.

Water is more likely to be present in the aqueous phase than in the organic phase containing carboxylic acids. Accordingly, after the completion of dehydration reaction, the aqueous phase is separated and the organic phase is recovered, and thus a dehydrated fluorocarboxylic acid solution is obtained.

In the present description, the term "concentrated sulfuric acid" refers to a sulfuric acid aqueous solution containing sulfuric acid at a concentration of 95% by mass or more. The concentrated sulfuric acid desirably has a sulfuric acid concentration of more than 95% by mass.

The quantity ratio of the fluorocarboxylic acid and concentrated sulfuric acid to be used in the reaction is not particularly limited, as long as it can maintain the later-described sulfuric acid concentration.

The dehydration step may be carried out under any suitable conditions with use of any suitable instruments, as long as the fluorocarboxylic acid is present in a liquid state. Dehydration is generally carried out at a temperature higher than the melting point of the fluorocarboxylic acid, normally at a temperature at least 3° C. higher than the melting point, and desirably at a temperature at least 5° C. higher than the melting point. For example, dehydration is carried out at a temperature 5 to 15° C. higher than the melting point. This condition can achieve substantially 100% dehydration in a comparatively short time. For example, in the case of preparing a linear C$_7$F$_{15}$COOH, dehydration at a temperature of 60 to 70° C. for two minutes can provide a dehydration product with the dehydration ratio of substantially 100%.

In the present invention, dehydration reaction may be carried out either in a batchwise manner or in a continuous manner. Dehydration reaction in a batchwise manner is carried out as follows. First, a fluorocarboxylic acid and concentrated sulfuric acid are sufficiently mixed. Next, the mixed solution is allowed to stand so as to be separated into an aqueous phase containing sulfuric acids and an organic phase containing a target fluorocarboxylic acid, and then, the organic phase is recovered. If needed, the obtained organic phase is again mixed with concentrated sulfuric acid and the mixture is placed still, so that the organic phase containing a smaller amount of water can be obtained. This operation is repeated until the water concentration in the organic phase has become lower than the desired level.

The dehydration step is a kind of extraction operation, and therefore, an organic phase may be continuously contacted with an aqueous phase in a liquid-liquid heterophase dispersed system including an organic phase and an aqueous phase. For example, an organic phase is desirably dispersed in an aqueous phase, or an aqueous phase is desirably dispersed in an organic phase. More specifically, the dehydration reaction can be carried out by, for example, dispersing liquid droplets of a mixture (organic phase) of a fluorocarboxylic acid and water as the dispersed phase in the concentrated sulfuric acid (aqueous phase) as the continuous phase. It promotes contact and material transfer between the aqueous phase as the continuous phase and the organic phase as the dispersed phase, so that dehydration reaction subsequently proceeds. The dispersed phase and the continuous phase may be reversed. The dehydration reaction is carried out by mixing the organic phase and the aqueous phase for a given period of time. The dehydrated fluorocarboxylic acid solution can be obtained by halting the mixing, subjecting the organic phase and the aqueous phase in the mixture to liquid separation, and collecting the organic phase.

Also, the dehydration step may include, in a liquid-liquid heterophase dispersed system including an aqueous phase and an organic phase, continuously contacting the organic phase with the aqueous phase, and separating the organic phase and the aqueous phase. FIG. 1 shows a static mixer, FIG. 2 shows a liquid-liquid separation column. A fluorocarboxylic acid solution and concentrated sulfuric acid are together fed into the static mixer 10 from feed opening 11 and 12. A dehydration reaction is carried out continuously in the static mixer 10 and both liquids are sent to the liquid-liquid separation column 20 from a discharge opening 14. Liquid-liquid separation of the both liquids fed from a feed opening 23 is carried out in the liquid-liquid separation column 20, and thereby a heavy liquid 21 and a light liquid 22 are obtained. A fluorocarboxylic acid phase separated in the liquid-liquid separation column 20 can be recovered.

In the dehydration step, dehydration can be continuously carried out by feeding the mixture and a sulfuric acid to a contacting column so that they flow countercurrent to each other. More specifically, dehydration may be carried out as follows. Either of the mixture and the concentrated sulfuric acid is fed as the light (i.e. lower density) liquid and the other material is fed as the heavy (i.e. higher density) liquid into a differential contacting extraction device, so to say "an extraction column (for example, Karr column extractor and the like)". Then, countercurrent contact is induced between the two liquids. The operation may be carried out with the aqueous phase serving as the continuous phase, and the organic phase serving as the dispersed phase, and vice versa.

In the dehydration step, a mixture containing a fluorocarboxylic acid and water may be contacted with diphosphorus pentoxide and/or zeolite at a temperature equal to or higher than the melting point of the fluorocarboxylic acid. In this case, concentrated sulfuric acid is not necessarily added. Namely, in the dehydration step, at least one material selected from the group consisting of concentrated sulfuric acid, diphosphorus pentoxide, and zeolites may be added to the mixture containing a fluorocarboxylic acid and water. Examples of zeolites include aluminosilicate.

The dehydrated fluorocarboxylic acid solution is obtainable after the dehydration reaction, and contains a fluorocarboxylic acid, sulfuric acid, and water. The dehydrated fluorocarboxylic acid solution desirably contains water at 1.0% by mass or less, because foaming and gel formation at purification can be avoided. If the water content is more than 1.0% by mass, a fluorocarboxylic acid may be ultimately obtained in lower purity and in lower yield. The water content is more desirably 0.7% by mass or less.

The sulfuric acid concentration is desirably 70.0 to 99.9% by mass in the dehydration step. The sulfuric acid concentration is a sulfuric acid concentration of an aqueous phase (concentration to the total weight of the aqueous phase) in the dehydration step. If the sulfuric acid concentration is too low, the dehydration reaction may not proceed sufficiently. The sulfuric acid concentration is more desirably 80.0 to 99.9% by mass, further desirably 90.0 to 99.9% by mass, and particularly desirably 95.0 to 99.9% by mass.

The mixture containing a fluorocarboxylic acid and water used in the dehydration step may be prepared by any suitable methods and may contain another component, as long as it does not adversely affect the process of the present invention. Examples of the mixture include a material obtainable from the process for obtaining a fluorocarboxylic acid by hydrolyzing or oxidizing fluorocarboxylic acid fluorides, fluorocarboxylates, or the like. The mixture may be obtained by following the method disclosed in Patent Documents 1 and 2, and the like.

In the purification step, the dehydrated fluorocarboxylic acid solution obtained in the dehydration step is purified. The purification may be carried out by distillation, crystallization, and the like. The distillation is desirably multi-stage distillation, because a fluorocarboxylic acid can be obtained in high purity.

In the process of the present invention, the multi-stage distillation can be adopted, and therefore, it is possible to prepare a fluorocarboxylic acid in high purity by separating the target component and impurities in high yield.

The fluorocarboxylic acid obtained by the process of the present invention may be treated with ammonia or alkali so as to be made into ammonium salts or alkali metal salts. The obtained material may be suitably used as a surfactant for polymerizing fluoromonomers and as a surfactant for stabilizing aqueous dispersion of fluoropolymers.

EFFECT OF THE INVENTION

The process of the present invention is as above described, and therefore, it is possible to prepare a fluorocarboxylic acid in high purity and in high yield.

BEST MODE FOR CARRYING OUT THE INVENTION

Figure 1:
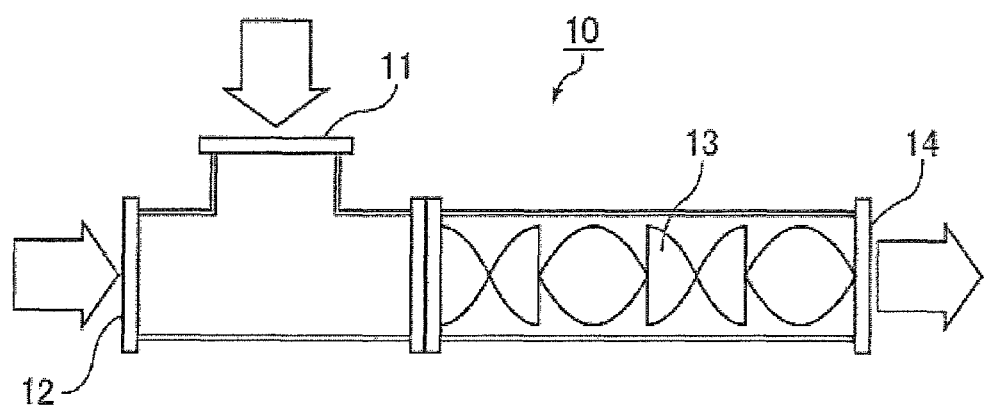
FIG. 1 is a schematic view showing a static mixer.

Examples and Comparative Examples are shown in the following, and the present invention is specifically described.
In the present examples, compositions of a top phase and a bottom phase are determined by the following method.
Concentration of the Fluorocarboxylic Acid
The concentration was measured by the HPLC method under the following conditions:
Column Shodex 5C8 4D (produced by SHOWA DENKO K.K),
Mobile phase: acetonitrile/0.6% by mass per chloric acid aqueous solution=1/1 (vol/vol),
Current speed: 1.0 ml/min.,
Feeding quantity: 100 µl,
Column temperature: 40° C.,
Detection: UV 210 nm.
Water Content
The water content was measured by the Karl Fischer method under the following conditions:
Reagent AOUAMICRON AKX/CXU (produced by Mitsubishi Chemical Corporation)
Measurement: Electometric titration
Sulfuric Acid Ion Concentration
The concentration was measured by ion chromatography under the following conditions:
Column: IonPac AS4A (4×250 mm) (produced by Nippon Dionex K.K.)
Mobile phase: sodium carbonate (2.5 mmol/l) and sodium hydrogen carbonate (1 mmol/l)
Current speed: 0.5 ml/min.,
Feeding quantity: 50 µl,
Detector: electric conductivity detector.

EXAMPLE 1

A 50-ml erlenmeyer flask with a stirrer was used. Concentrated sulfuric acid (sulfuric acid concentration of 98% by mass, 10 g) was conditioned to have a temperature of 70° C. in the flask and 10 g of $C_7F_{15}COOH$ mixture (prepared by the method disclosed in Patent Document 1, a mixture containing 93.3% by mass of $C_7F_{15}COOH$, 6.3% by mass of water, and 0.4% by mass of sulfuric acids) was added thereto. Then, the mixture was stirred for 10 minutes and allowed to stand for 60 minutes, so that the mixture was separated into a top phase and a bottom phase. The top phase was an organic phase containing $C_7F_{15}COOH$ and the bottom phase was an aqueous phase containing sulfuric acids and water.

The top phase (dehydrated fluorocarboxylic acid ($C_7F_{15}COOH$)) was separated and recovered, and its composition was determined. The following results were obtained.
$C_7F_{15}COOH$ 99% by mass
$H_2O$ 6800 ppm by mass The composition of the bottom phase was determined and the following results were obtained.
$C_7F_{15}COOH$ 1500 ppm by mass
$H_2SO_4$ 95% by mass Multistage distillation was carried out on 200 g of the top phase (dehydrated fluorocarboxylic acid) in a 10-tray Oldershaw distillation column, so that the purified fluorocarboxylic acid was obtained. The yield was 99.3% by mass. A sulfuric acid ion in the obtained fluorocarboxylic acid distillate was below the detection limit.

EXAMPLE 2

The same procedure as that in Example 1 was conducted, except that $C_5F_{11}COOH$ mixture (prepared by the method disclosed in Patent Document 1, a mixture containing 93.8% by mass of $C_5F_{11}COOH$, 6.0% by mass of water, and 0.2% by mass of sulfuric acids) was used and the temperature was changed to 30° C.

The top phase (dehydrated fluorocarboxylic acid ($C_5F_{11}COOH$)) was separated and recovered, and its composition was determined. The following results were obtained.
$C_5F_{11}COOH$ 99% by mass
$H_2O$ 400 ppm by mass The composition of the bottom phase was determined and the following result was obtained.
$H_2SO_4$ 94% by mass Multistage distillation was carried out on 200 g of the top phase (dehydrated fluorocarboxylic acid) in a 10-tray Oldershaw distillation column, so that the purified fluorocarboxylic acid was obtained. The yield was 99.7% by mass. A sulfuric acid ion in a fluorocarboxylic acid distillate was below the detection limit.

EXAMPLE 3

The same procedure as that in Example 1 was conducted, except that $CF_3OCF(CF_3)CF_2OCF(CF_3)COOH$ mixture (prepared by the method disclosed in Patent Document 1, a mixture containing 91.4% by mass of $CF_2OCF(CF_3)CF_2OCF(CF_3)COOH$, 8.2% by mass of water, and 0.4% by mass of sulfuric acids) was used and the temperature was changed to 30° C.

The top phase (dehydrated fluorocarboxylic acid ($CF_3OCF(CF_3)CF_2OCF(CF_3)COOH$)) was separated and recovered, and its composition was determined. The following results were obtained.
$CF_3OCF(CF_3)CF_2OCF(CF_3)COOH$ 99% by mass
$H_2O$ 450 ppm by mass The composition of the bottom phase was determined and the following result was obtained.
$H_2SO_4$ 91% by mass Multistage distillation was carried out on 200 g of the top phase (dehydrated fluorocarboxylic acid) in a 10-tray Oldershaw distillation column, so that the purified fluorocarboxylic acid was obtained. The yield was 99.5% by mass. A sulfuric acid ion in a fluorocarboxylic acid distillate was below the detection limit.

REFERENCE EXAMPLES 1 and 2

The same procedure as that in Example 1 was conducted in each Reference Example, except that the amount of concentrated sulfuric acid to be used for dehydration was changed. Table 1 shows the results of analysis of the organic phase and the aqueous phase obtained after dehydration.

EXAMPLE 4

The same procedure as that in Example 1 was conducted, except that the amount of concentrated sulfuric acid to be used for dehydration was changed. In Example 4, the top phase was an aqueous phase containing sulfuric acids and water, and the bottom phase was an organic phase containing $C_7F_{15}COOH$. Table 1 shows the results of analysis of the organic phase and the aqueous phase obtained after dehydration.

Multistage distillation was carried out on 200 g of the organic phase (dehydrated fluorocarboxylic acid) in a 10-tray Oldershaw distillation column, so that the purified fluorocarboxylic acid was obtained. The yield represented table 1. A sulfuric acid ion in the obtained fluorocarboxylic acid distillate was below the detection limit.

REFERENCE EXAMPLES 3 to 4

The same procedure as that in Example 1 was conducted in each Reference Example, except that $C_5F_{11}COOH$ mixture (prepared by the method disclosed in Patent Document 1, a mixture containing 93.8% by mass of $C_5F_{11}COOH$, 6.0% by mass of water, and 0.2% by mass of sulfuric acids) was used and the temperature was changed to 30° C. Table 1 shows the results of analysis of the organic phase and the aqueous phase obtained after dehydration.

EXAMPLE 5

The same procedure as that in Example 1 was conducted in each Reference Example, except that $C_5F_{11}COOH$ mixture (prepared by the method disclosed in Patent Document 1, a mixture containing 93.8% by mass of $C_5F_{11}COOH$, 6.0% by mass of water, and 0.2% by mass of sulfuric acids) was used and the temperature was changed to 30° C. In Example 5, the top phase was an aqueous phase containing sulfuric acids and water, and the bottom phase was an organic phase containing $C_5F_{11}COOH$. Table 1 shows the results of analysis of the organic phase and the aqueous phase obtained after dehydration.

Multistage distillation was carried out on 200 g of the organic phase (dehydrated fluorocarboxylic acid) in a 10-tray Oldershaw distillation column, so that the purified fluorocarboxylic acid was obtained. The yield represented table 1. A sulfuric acid ion in the obtained fluorocarboxylic acid distillate was below the detection limit.

REFERENCE EXAMPLES 5 and 6

The same procedure as that in Example 1 was conducted in each Reference Example, except that $CF_3OCF(CF_3)CF_2OCF(CF_3)COOH$ mixture (prepared by the method disclosed in Patent Document 1, a mixture containing 91.4% by mass of $CF_3OCF(CF_3)CF_2OCF(CF_3)COOH$, 8.2% by mass of water, and 0.4% by mass of sulfuric acids) was used and the temperature was changed to 30° C. In both of Reference Examples, the top phase was an organic phase containing $CF_3OCF(CF_3)CF_2OCF(CF_3)COOH$, and the bottom phase was an aqueous phase containing sulfuric acids and water. Table 1 shows the results of analysis of the organic phase and the aqueous phase obtained after dehydration.

EXAMPLE 6

The same procedure as that in Reference Example 5 was conducted, except that the amount of concentrated sulfuric acid to be used for dehydration was changed.

Multistage distillation was carried out on 200 g of the organic phase (dehydrated fluorocarboxylic acid) in a 10-tray Oldershaw distillation column, so that the purified fluorocarboxylic acid was obtained. Table 1 shows the yield. A sulfuric acid ion in the obtained fluorocarboxylic acid distillate was below the detection limit.

TABLE 1

| Reference Examples | Additive amount of concentrated sulfuric acid (g) | Concentration of water in organic phase (ppm by mass) | Concentration of sulfuric acid in aqueous phase (% by mass) | yields (% by mass) |
|---|---|---|---|---|
| Reference Example 1 | 7 | 5800 | 93 | — |
| Reference Example 2 | 5 | 8100 | 91 | — |
| Example 4 | 3 | 9500 | 86 | 98.4 |
| Reference Example 3 | 7 | 700 | 92 | — |
| Reference Example 4 | 5 | 1500 | 89 | — |
| Example 5 | 3 | 2500 | 84 | 99.3 |
| Reference Example 5 | 20 | 550 | 95 | — |
| Reference Example 6 | 5 | 1200 | 83 | — |
| Example 6 | 3 | 5000 | 75 | 98.0 |

REFERENCE EXAMPLE 7

In order to confirm that multistage distillation of the dehydrated carboxylic acid can provide a carboxylic acid in high purity, multistage distillation was carried out on the mixed solution containing 200 g of $CF_3OCF(CF_3)CF_2OCF(CF_3)COOH$, 6.0 g of $C_7F_{15}COOH$, and 6.0 g of $C_5F_{11}COOH$, and having a water concentration of 600 ppm by mass. Examination was carried out in a 15-tray Oldershaw distillation column, and the distillate was separated into 8 parts and respectively collected. Table 2 shows the results of analysis of $C_5F_{11}COOH$ concentration and $C_7F_{15}COOH$ concentration of each distillate.

TABLE 2

| Distillates | $C_5F_{11}COOH$ (% by mass) | $C_7F_{15}COOH$ (% by mass) |
|---|---|---|
| 1 | 9.6 | 0 |
| 2 | 7.0 | 0 |
| 3 | 4.5 | 0 |
| 4 | 2.9 | 0 |
| 5 | 0 | 0 |
| 6 | 0 | 0 |
| 7 | 0 | 0.01 |
| 8 | 0 | 0.02 |

As shown in Table 2, $C_5F_{11}COOH$ and $C_7F_{15}COOH$ were not contained in distillates 5 and 6. Accordingly, it was found out that $C_5F_{11}COOH$ can be adequately removed as the first distillate and $C_7F_{15}COOH$ can be removed as the latter distillate. Namely, it was possible to obtain $CF_3OCF(CF_3)CF_2OCF(CF_3)COOH$ in high purity.

COMPARATIVE EXAMPLE

Multistage distillation (10 trays) was conducted on 200 g of $C_7F_{15}COOH$ mixture used in Example 1. However, foaming was found in the column and distillation could not be carried out. In the same manner, multistage distillation was respectively conducted on 200 g of $C_5F_{11}COOH$ mixture used in Example 2 and 200 g of $CF_3OCF(CF_3)CF_2OCF(CF_3)COOH$ mixture used in Example 3. Foaming in the column was found also in each of these cases, and distillation could not be carried out.

EXAMPLE 7

Figure 2:
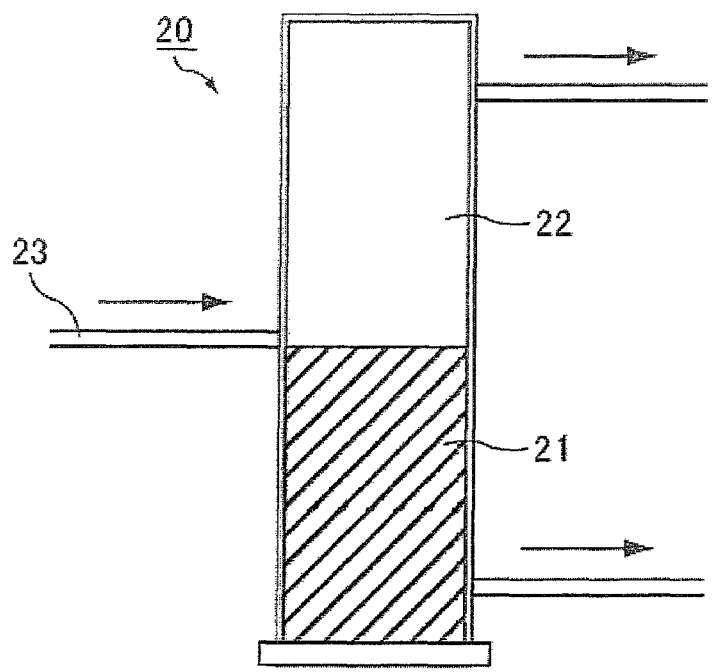
FIG. 2 is a schematic view showing a liquid-liquid separation column.

In Example 7, a static mixer 10 shown in FIG. 1 and a liquid-liquid separation column 20 shown in FIG. 2 were used. A static mixer with 12 pieces of elements 13 produced by Noritake Co., Limited was used as the static mixer. A column measuring 25 mm in diameter and 1300 mm in length was used as the liquid-liquid separation column.

A fluorocarboxylic acid solution containing 93.3% by mass of $C_5F_{11}COOH$, 6.3% by mass of $H_2O$, and 0.4% by mass of sulfuric acid, and concentrated sulfuric acid were together fed into the static mixer 10 from feed opening 11 and 12 at a flow rate of 25 cc/min. A dehydration reaction was carried out continuously in the static mixer 10 and both liquids were sent to the liquid-liquid separation column 20 from a discharge opening 14. Liquid-liquid separation of the both liquids fed from a feed opening 23 was carried out in the liquid-liquid separation column 20, and thereby a heavy liquid 21 and a light liquid 22 were obtained. A fluorocarboxylic acid phase (light liquid) separated in the liquid-liquid separation column 20 was recovered and the composition thereof was determined. The following result was obtained.

$C_5F_{11}COOH$ 99.2% by mass
$H_2O$ 340 ppm by mass

Multistage distillation was carried out on 200 g of the light liquid (dehydrated fluorocarboxylic acid) in a 10-tray Oldershaw distillation column, so that the purified fluorocarboxylic acid was obtained. The yield was 99.3% by mass. A sulfuric acid ion in the obtained fluorocarboxylic acid distillate was below the detection limit.

REFERENCE EXAMPLES 8 to 10

In each Example, a fluorocarboxylic acid phase was recovered in the same manner as in Example 7, except that the flow rate of the fluorocarboxylic acid solution. The composition thereof was determined and the results shown in Table 3 were obtained.

TABLE 3

| | flow rate (cc/min) | | Compositon of Dehydration fluorocarboxylic acid phase | |
|---|---|---|---|---|
| | fluoro-carboxylic acid | concen-trated sulfuric acid | $C_5F_{11}COOH$ (% by mass) | $H_2O$ (ppm by mass) |
| Reference Example 8 | 90 | 30 | 97.8 | 670 |
| Reference Example 9 | 40 | 25 | 98.6 | 370 |
| Reference Example 10 | 15 | 45 | 99.1 | 450 |

EXAMPLE 8

A fluorocarboxylic acid phase was recovered in the same manner as in Example 7, except that the fluorocarboxylic acid solution having the below composition was used and the flow rate of the fluorocarboxylic acid solution and the concentrated sulfuric acid was changed. The composition thereof was determined and the results shown in Table 4 were obtained.

Composition of the fluorocarboxylic acid solution
$CF_3OCF(CF_3)CF_2OCF(CF_3)COON$ 92.2% by mass
$H_2O$ 7.5% by mass
$H_2SO_4$ 0.3% by mass Multistage distillation was carried out on 200 g of the light liquid (dehydrated fluorocarboxylic acid) in a 10-tray Oldershaw distillation column, so that the purified fluorocarboxylic acid was obtained. The yield was 99.5% by mass. A sulfuric acid ion in the obtained fluorocarboxylic acid distillate was below the detection limit.

REFERENCE EXAMPLES 11 to 13

In each Example, a fluorocarboxylic acid phase was recovered in the same manner as in Example 8, except that the flow rate of the fluorocarboxylic acid solution and the concentrated sulfuric acid was changed. The composition thereof was determined and the results shown in Table 4 were obtained.

TABLE 4

| | flow rate (cc/min) | | Compositon of Dehydration fluorocarboxylic acid phase | |
|---|---|---|---|---|
| | fluoro-carbox-ylic acid | concen-trated sulfuric acid | $CF_3OCFCF_3CF_2OCF(CF_3)COOH$ (% by mass) | $H_2O$ (ppm by mass) |
| Example 8 | 25 | 25 | 99.3 | 230 |
| Reference Example 11 | 90 | 30 | 96.8 | 900 |
| Reference Example 12 | 45 | 25 | 98.5 | 510 |
| Reference Example 13 | 15 | 45 | 99.5 | 170 |

EXAMPLE 9

A fluorocarboxylic acid phase was recovered in the same manner as in Example 7, except that the fluorocarboxylic acid solution having the below composition was used, and its composition was determined. The following results were obtained.

The composition of the fluorocarboxylic acid solution
$C_7F_{15}COOH$ 92.6% by mass
$H_2O$ 6.8% by mass
$H_2SO_4$ 0.6% by mass
The composition of the fluorocarboxylic acid phase
$C_7F_{15}COOH$ 98.9% by mass
$H_2O$ 0.6% by mass Multistage distillation was carried out on 200 g of the light liquid (dehydrated fluorocarboxylic acid) in a 10-tray Oldershaw distillation column, so that the purified fluorocarboxylic acid was obtained. The yield was 99.3% by mass. A sulfuric acid ion in the obtained fluorocarboxylic acid distillate was below the detection limit.

EXAMPLE 10

Figure 3:
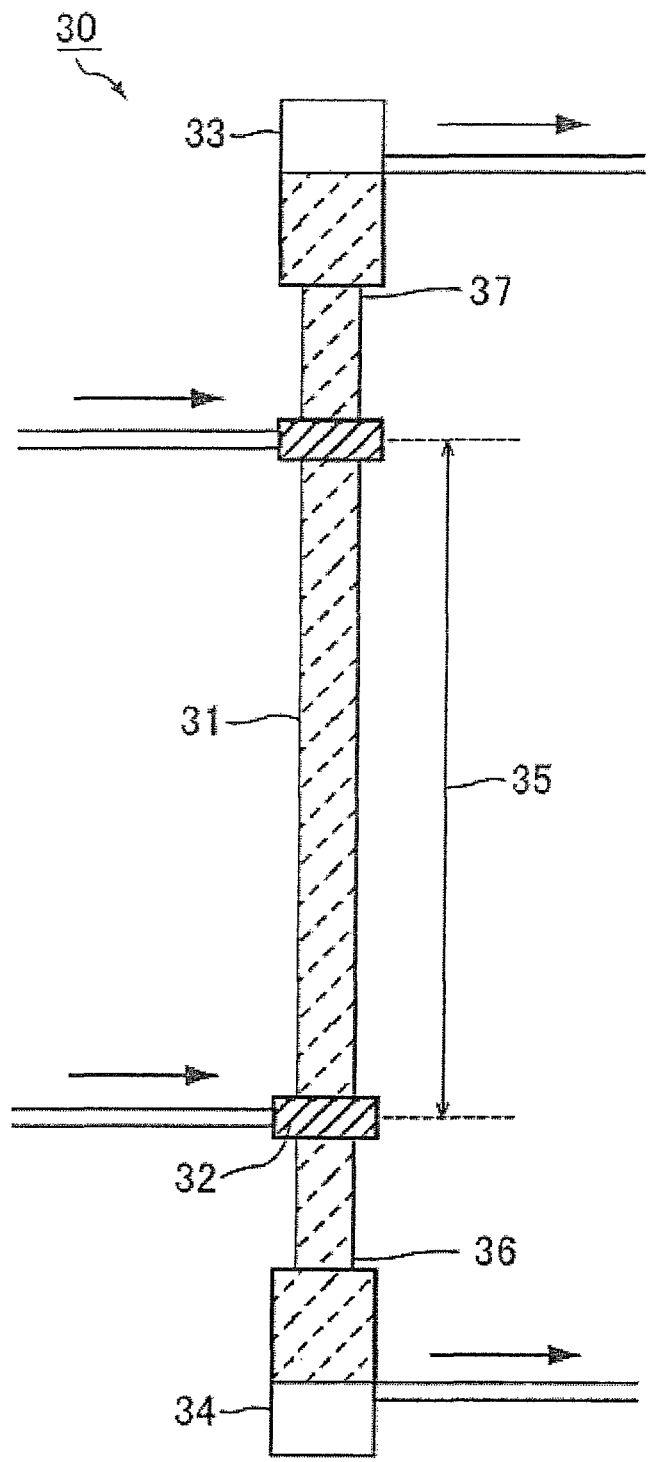
FIG. 3 is a schematic view showing a Karr column extractor.

The Karr column extractor 30 shown in the FIG. 3 was used in Example 10. The column has a cylindrical section 31 (length, 3.0 m) of 2.5 cm diameter, above and below which are positioned receptacles 33 and 34 as decanters. At the interior of the cylindrical section 31, disk-like plates (55 plates positioned at 5 cm intervals) are moved vertically so as to agitate the liquid within the cylindrical section.

A concentrated sulfuric acid solution (98% by mass) was continuously fed as the heavy liquid at a flow rate of 150 cc/min from the vicinity of the top end 37 of the cylindrical section. A fluorocarboxylic acid solution ($C_5F_{11}COOH$ 93% by mass, $H_2O$ 6.6% by mass, $H_2SO_4$ 0.4% by mass) was continuously fed as the light liquid at a flow rate of 150 cc/min from a feed opening 32 provided at a position 0.6 m from the bottom end 36 of the cylindrical section. The a fluorocarboxylic acid solution rose in the form of liquid droplets within the aqueous sulfuric acid solution.

The water in the fluorocarboxylic acid solution was present in the fluorocarboxylic acid phase serving as the dispersed organic phase, but during continuously extracted (i.e., dehydrated) at the dehydrating zone 35 by the sulfuric acid solution rising up through the column. The liquid droplets of fluorocarboxylic acid phase (dispersed phase) that had descended coalesce in the decanter 33 at the top of the column and liquid separation occurred, resulting in the formation of an interface with the aqueous sulfuric acid solution.

The fluorocarboxylic acid phase that formed in the decanter 33 at the top of the column was recovered, and its composition was determined. The following results were obtained.
$C_5F_{11}COOH$ 98.1% by mass
$H_2O$ 2260 ppm by mass
$H_2SO_4$ 1.7% by mass Multistage distillation was carried out on 200 g of the light liquid (dehydrated fluorocarboxylic acid) in a 10-tray Oldershaw distillation column, so that the purified fluorocarboxylic acid was obtained. The yield was 98.2% by mass. A sulfuric acid ion in the obtained fluorocarboxylic acid distillate was below the detection limit.

EXAMPLE 11

A fluorocarboxylic acid phase was recovered in the same manner as in Example 10, except that the fluorocarboxylic acid solution having the below composition was used, and its composition was determined. The following results were obtained.

The Composition of the Fluorocarboxylic Acid Solution
$CF_3OCF(CF_3)CF_2OCF(CF_3)COOH$ 95.0% by mass
$H_2O$ 4.7% by mass
$H_2SO_4$ 0.3% by mass The Composition of the Fluorocarboxylic Acid Phase
$CF_3OCF(CF_3)CF_2OCF(CF_3)COOH$ 98.8% by mass
$H_2O$ 1530 ppm by mass
$H_2SO_4$ 1.0% by mass Multistage distillation was carried out on 200 g of the light liquid (dehydrated fluorocarboxylic acid) in a 10-tray Oldershaw distillation column, so that the purified fluorocarboxylic acid was obtained. The yield was 98.3% by mass. A sulfuric acid ion in the obtained fluorocarboxylic acid distillate was below the detection limit.

EXAMPLE 12

A fluorocarboxylic acid phase was recovered in the same manner as in Example 10, except that the fluorocarboxylic acid solution having the below composition was used, and its composition was determined. The following results were obtained.

The Composition of the Fluorocarboxylic Acid Solution
$C_7F_{15}COOH$ 92.6% by mass
$H_2O$ 6.8% by mass
$H_2SO_4$ 0.6% by mass The Composition of the Fluorocarboxylic Acid Phase
$CF_3OCF(CF_3)CF_2OCF(CF_3)COOH$ 98.0% by mass
$H_2O$ 0.8% by mass Multistage distillation was carried out on 200 g of the light liquid (dehydrated fluorocarboxylic acid) in a 10-tray Oldershaw distillation column, so that the purified fluorocarboxylic acid was obtained. The yield was 98.1% by mass. A sulfuric acid ion in the obtained fluorocarboxylic acid distillate was below the detection limit.

INDUSTRIAL APPLICABILITY

The process of the present invention can be suitably used as a process for preparing a fluorocarboxylic acid useful as a surfactant for polymerization.

| EXPLANATION OF NUMERALS AND SYMBOLS | |
|---|---|
| 10 | static mixer |
| 11, 12, 23 | feed opening |
| 13 | element |
| 14 | discharge opening |
| 20 | liquid-liquid separation column |
| 21 | heavy liquid |
| 22 | light liquid |
| 30 | Karr column extractor |
| 31 | cylindrical section |
| 33, 34 | receptacle |
| 35 | dehydrating zone |
| 36 | bottom end of cylindrical section |
| 37 | top end of cylindrical section |

The invention claimed is:

1. A process for preparing a fluorocarboxylic acid, which comprises:
    a dehydration step of removing from a mixture containing a fluorocarboxylic acid and water at least a part of said water to obtain a dehydrated fluorocarboxylic acid solution; and
    a purification step of purifying said dehydrated fluorocarboxylic acid solution,
    wherein the dehydration step includes adding concentrated sulfuric acid to the mixture containing a fluorocarboxylic acid and water, and
    wherein the dehydration step proceeds in a liquid-liquid heterophase dispersed system including an aqueous phase and an organic phase, and said aqueous phase has a sulfuric acid concentration of 70.0 to 99.9% by mass.

2. The process of claim 1, wherein the dehydration step includes, in a liquid-liquid heterophase dispersed system including an aqueous phase and an organic phase, continuously contacting the organic phase with the aqueous phase.

3. The process of claim 1, wherein the dehydration step includes, in a liquid-liquid heterophase dispersed system including an aqueous phase and an organic phase, continuously contacting the organic phase with the aqueous phase, and separating the organic phase and the aqueous phase.

4. The process of claim 1, wherein the dehydration step includes continuously carrying out dehydration by feeding the said mixture and a sulfuric acid to a contacting column so that they flow countercurrent to each other.

* * * * *